United States Patent
Markert et al.

(10) Patent No.: US 6,376,457 B1
(45) Date of Patent: Apr. 23, 2002

(54) PHENOKETALS AND THE USE THEREOF AS ODORIFEROUS SUBSTANCES

(75) Inventors: Thomas Markert, Monheim; Ralph Nemitz, Juechen, both of (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/402,285

(22) PCT Filed: Mar. 27, 1998

(86) PCT No.: PCT/EP98/01815

§ 371 Date: Oct. 1, 1999

§ 102(e) Date: Oct. 1, 1999

(87) PCT Pub. No.: WO98/45236

PCT Pub. Date: Oct. 15, 1998

(30) Foreign Application Priority Data

Apr. 5, 1997 (DE) .......................... 197 14 041

(51) Int. Cl.[7] .................................. A61K 7/46
(52) U.S. Cl. .................... 512/20; 512/25; 512/26; 512/27; 424/76.4; 510/101; 549/347; 549/356
(58) Field of Search ............................. 512/20, 25, 26, 512/27; 424/76.4; 510/101; 549/347, 356

(56) References Cited

U.S. PATENT DOCUMENTS

| | | | | |
|---|---|---|---|---|
| 3,166,600 A | * | 1/1965 | Lorette et al. | 568/591 |
| 3,262,938 A | * | 7/1966 | Hardie et al. | 546/207 |
| 4,614,611 A | | 9/1986 | Sprecker | 252/528 R |
| 5,084,440 A | * | 1/1992 | Baudin et al. | 512/12 |

FOREIGN PATENT DOCUMENTS

| EP | 0 052 775 | 6/1982 |
|---|---|---|
| EP | 52775 | * 6/1982 |

OTHER PUBLICATIONS

"Synthesis of 2–Naphthyl Vinyl ethers," Wolff, Thomas; Phys. Chem.; Univ. Siegen, (10), 847–9, 1980. (abstract).*
"Study of the Polycyclocondensation of Ketals of Acetyl–Aromatic Compounds," Korshak, V.V.; Inst. Element oorg. Soedin, 21(7), 1601–7, 1979 (abstract).*
Synthetic Communications, vol. 27, No. 1, XP002073790, pp. 11–15 (19997).

* cited by examiner

*Primary Examiner*—Jill Warden
*Assistant Examiner*—Monique T. Cole
(74) *Attorney, Agent, or Firm*—John E. Drach; Henry E. Millson, Jr.

(57) ABSTRACT

Phenone ketals corresponding to formula (I):

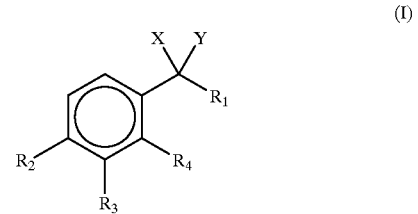

where X and Y independently of one another represent methoxy, ethoxy, propoxy or butoxy groups and $R_1$ is a methyl, ethyl or propyl group, $R_2$ is hydrogen or a methyl, ethyl, isopropyl, tert.butyl or methoxy group, $R_3$ is hydrogen or a methoxy group and $R_4$ is hydrogen or a methyl group; their use as a component of perfumes; and perfume compositions containing them.

20 Claims, No Drawings

PHENOKETALS AND THE USE THEREOF AS ODORIFEROUS SUBSTANCES

FIELD OF THE INVENTION

This invention relates to phenone ketals having a special structure and to their use as perfumes.

BACKGROUND OF THE INVENTION

Judging by demand, many natural perfumes are available in totally inadequate quantities. For example, 5,000 kg of rose blossoms are required to obtain 1 kg of rose oil. The consequences are extremely limited annual world production and a high price. Accordingly, it is clear that there is a constant need in the perfume industry for new perfumes with interesting fragrance notes in order to extend the range of naturally available perfumes, to make the necessary adaptations to changing fashion trends and to be able to meet the steadily increasing demand for odor enhancers for products of everyday use, such as cosmetics and cleaners.

Accordingly, it is clear that there is a constant need in the perfume industry for new perfumes with interesting fragrance notes in order to extend the range of naturally available perfumes, to make the necessary adaptations to changing fashion trends and to be able to meet the steadily increasing demand for odor enhancers for products of everyday use, such as cosmetics and cleaners.

In addition, there is generally a constant need for synthetic perfumes which can be favorably produced in a consistent quality and which have desirable olfactory properties, i.e. pleasant, near-natural and qualitatively new odor profiles of adequate intensity, and which are capable of advantageously influencing the fragrance of cosmetic and consumer products. In other words, there is a constant need for compounds which have characteristic new odor profiles coupled with high staying power, intensity of odor and emanative power.

SUMMARY OF THE INVENTION

It has now been found that special phenone ketals corresponding to formula (I) below excellently satisfy the requirements mentioned above in every respect and may advantageously be used as perfumes with differently nuanced odor notes characterized by high staying power.

In a first embodiment, the present invention relates to phenone ketals corresponding to general formula (I):

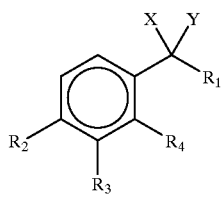

(I)

where X and Y independently of one another represent methoxy, ethoxy, propoxy or butoxy groups and $R_1$ is a methyl, ethyl or propyl group, $R_2$ is hydrogen or a methyl, ethyl, isopropyl, tert.butyl or methoxy group, $R_3$ is hydrogen or a methoxy group and $R_4$ is hydrogen or a methyl group.

In one preferred embodiment of the invention, the phenone ketals corresponding to general (Ia):

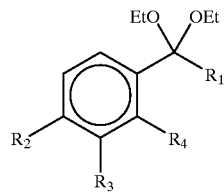

(Ia)

where $R_1$ is a methyl or ethyl group, $R_2$ is a methyl, tert.butyl or methoxy group, $R_3$ is hydrogen or a methoxy group and $R_4$ is hydrogen or a methyl group.

In another embodiment, the present invention relates to the use of phenone ketals corresponding to general formula (I) as perfumes. The compounds (Ia) are preferably used, the compound 1-(1,1-diethoxyethyl)-2,4-dimethyl benzene, i.e. the diethyl ketal of 2,4-dimethyl acetophenone, being particularly preferred.

DESCRIPTION OF THE PREFERRED EMBODIMENTS

The carbonyl compounds according to the invention are distinguished by an odor characteristic in which flowery notes reminiscent of anthranilate, ylang and tuberose are dominant. They show excellent stability in formulations used for cosmetics and consumer perfumery.

The compounds (I) are prepared by syntheses known per se in organic chemistry. Their synthesis is carried out, for example, by stirring the ketones which are dissolved in the required alcohol and which are used in excess in the presence of dehydrating agents which may be used both in catalytic quantities (0.01 to 0.2 mol-%) and in molar quantities (where molecular sieves are used), based on the ketones. Suitable dehydrating agents are, for example, sulfates, such as magnesium, sodium or potassium sulfates and hydrogen sulfates, or sulfonic acids, such as for example p-toluenesulfonic acid, pyridinium tosylate, etc. and molecular sieves (preferably with a pore diameter of ca. 4 Angstroms).

The ketals according to the invention can be obtained in very pure form by distilling off the excess alcohol and fractionating the crude product.

In perfume compositions, the compounds (I) enhance harmony and emanation and also persistence, the quantities used being adapted to the particular fragrance note required taking the other ingredients of the composition into account.

The fact that the carbonyl compounds (I) have flowery, anthranilate, ylang and tuberose notes was not foreseeable and, accordingly, is further confirmation of the general experience that the olfactory properties of known perfumes are not always an indication of the properties of structurally related compounds because neither the mechanism of odor perception nor the influence of chemical structure on odor perception has been adequately researched, so that it is not normally possible to predict whether a modified structure of known perfumes will in fact lead to a change in the olfactory properties and whether these changes will be positive or negatively evaluated.

By virtue of their odor profile, the compounds corresponding to formula (I) are also particularly suitable for modifying and enhancing known compositions. Their extraordinary intensity of odor is particularly emphasized, contributing quite generally towards refining the composition.

The compounds corresponding to formula (I) may be combined with many known perfume ingredients, for example other perfumes of natural, synthetic or partly synthetic origin, essential oils and plant extracts. The range of natural perfumes can encompass both high volatility and medium to low volatility components while the range of synthetic perfumes can encompass representatives of virtually all classes of compounds. The following are examples:

(a) natural products, such as tree moss absolue, basil oil, citrus oils, such as bergamot oil, mandarin oil, etc., mastix absolue, myrtle oil, palmarosa oil, patchouli oil, petitgrain oil, absinth oil, myrrh oil, olibanum oil, (b) alcohols, such as farnesol, geraniol, linalool, nerol, phenylethyl alcohol, rhodinol, cinnamic alcohol, sandalore [3-methyl-5-(2, 2, 3-trimethylcyclopent-3-en-1-yl)-pentan-2-ol], sandela [3-isocamphyl-(5)-cyclohexanol], (c) aldehydes, such as citral, Helional®, α-hexyl cinnamic aldehyde, hydroxycitronellal, Lilial® [p-tert.butyl-α-methyl dihydrocinnamic aldehyde], methyl nonyl acetaldehyde, (d) ketones, such as allyl ionone, α-ionone, β-ionone, isoraldein, methyl ionone, (e) esters, such as allylphenoxyacetate, benzyl salicylate, cinnamyl propionate, citronellyl acetate, decyl acetate, dimethyl benzylcarbinyl acetate, ethyl acetoacetate, hexenyl isobutyrate, linalyl acetate, methyl dihydrojasmonate, vetiveryl acetate, cyclohexyl salicylate, (f) lactones, such as gamma-undecalactone, 1-oxaspiro-[4.4]-nonan-2-one, and various other components often used in perfumery, such as musk, indole, p-menthane-8-thiol-3-one, methyl eugenol, Ambroxan.

Also remarkable is the way in which the compounds (I) round off and harmonize the odor notes of a broad range of known compositions without unpleasantly dominating them. 1-(1,1-dioxyethyl)-2,4-dimethylbenzene, i.e. the diethylketal of 2,4dimethylacetophenone, is particularly emphasized in this regard.

The percentages by weight of the compounds according to the invention or mixtures thereof which can be used in perfume compositions range from 1 to 70% by weight, based on the mixture as a whole. Mixtures of the compounds (I) according to the invention and compositions of this type may be used both for perfuming cosmetic preparations, such as lotions, cremes, shampoos, soaps, emollients, powders, aerosols, toothpastes, mouthwashes, deodorants, and in alcohol-based perfumery (for example colognes, toilet waters, extracts). They may also be used for perfuming industrial products, such as detergents and cleaners, fabric softeners and textile treatment compositions. For perfuming these various products, the compositions are added in an olfactorily effective quantity, more particularly in a concentration of 0.05 to 2% by weight, based on the product as a whole. However, these values are not intended to represent particular limits because the experienced perfumer can obtain effects with lower concentrations or can create new complexes with even higher concentrations.

The following Examples are intended to illustrate the invention without limiting it in any way.

Examples

Example 1

1-(1,1-diethoxyethyl)-2,4-dimethyl benzene
Materials:
1) 97.3 g (0.66 mol) 2,4-dimethyl acetophenone (Fluka)
2) 117.3 g (0.79 mol) triethyl orthoformate (Fluka)
3) 123.7 mg potassium hydrogen sulfate (Merck)
4) 600 ml ethanol, water-free (technical quality)
Method:

Substances 1) to 4) were introduced into a 1-liter three-necked flask and stirred for 78 hours at 20° C. in the absence of moisture (drying tube filled with silica gel) while dry nitrogen (ca. 2 I/h) was passed through. Thereafter no more educt could be detected in the mixture by GLC. For working up, the catalyst was neutralized with 2 ml of sodium methylate solution (30% in methanol) and the mixture was stirred for 15 minutes. The ethanol was then removed in a rotary evaporator and the remaining 150.9 g of light-brown residue was used for distillation in a 15 cm packed column (Braunschweig coils). 133.5 g of main runnings with a boiling point of 73–75° C./0.1 mbar were obtained. The gas chromatographic purity was 94.6%.

Odor description: musk, anthranilate, sulfur rubber note

Example 2

(1,1-diethoxybutyl)-benzene
Materials:
1) 148.0 g (1.0 mol) phenyl propyl ketone (Fluka)
2) 177.8 g (1.2 mol) triethyl orthoformate (Fluka)
3) 187.4 mg potassium hydrogen sulfate (Merck)
4) 600 ml ethanol, water-free (technical quality)
Method:

Substances 1) to 4) were introduced into a 1-liter three-necked flask and stirred for 78 hours at 20° C. in the absence of moisture (drying tube filled with silica gel) while dry nitrogen (ca. 2 I/h) was passed through. Thereafter only 6% of educt could be detected in the mixture by GLC. For working up, the catalyst was neutralized with 2 ml of sodium methylate solution (30% in methanol) and the mixture was stirred for 15 minutes. The ethanol was then removed in a rotary evaporator and the remaining 195.4 g of light orange liquid was used for distillation in a 15 cm packed column (Braunschweig coils). 182.9 g of main runnings with a boiling point of 74–78° C./0.1 mbar were obtained. The gas chromatographic purity was 88.9%.

Odor description: fresh, flowery, EdT, citrus note.

Example 3

1-(1,1-diethoxyethyl)-3,4-dimethoxybenzene
Materials:
1) 180.0 g (1.0 mol) 3,4-dimethcxyacetophenone (Merck)
2) 177.7 g (1.2 mol) triethyl orthoformate (Fluka)
3) 187.4 mg potassium hydrogen sulfate (Merck)
4) 600 ml ethanol, water-free (technical quality)
Method:

Substances 1) to 4) were introduced into a 1-liter three-necked flask and stirred for 20 hours at 20° C. in the absence of moisture (drying tube filled with silica gel) while dry nitrogen (ca. 2 I/h) was passed through. Thereafter only 10% of educt could be detected in the mixture by GLC. For working up, the catalyst was neutralized with 2 ml of sodium methylate solution (30% in methanol) and the mixture was stirred for 15 minutes. The ethanol was then removed in a rotary evaporator and the remaining 254.0 g of brown liquid was used for distillation in a 15 cm packed column (Braunschweig coils). 197.3 g of main runnings with a boiling point of 102–103° C./0.1 mbar were obtained. The gas chromatographic purity was 99.7%.

Odor description: fresh, flowery, dihydrojasmonate note

Example 4

1-(1,1-diethoxyethyl)-4-ethylbenzene

Materials:
1) 148.0 g (1.0 mol) 4-ethylacetophenone (Aldrich)
2) 177.7 g (0.79 mol) triethyl orthoformate (Fluka)
3) 187.4 mg potassium hydrogen sulfate (Merck)
4) 600 ml ethanol, water-free (technical quality)

Method:
Substances 1) to 4) were introduced into a 1-liter three-necked flask and stirred for 20 hours at 20° C. in the absence of moisture (drying tube filled with silica gel) while dry nitrogen (ca. 2 I/h) was passed through. Thereafter only product could be detected in the mixture by GLC. For working up, the catalyst was neutralized with 2 ml of sodium methylate solution (30% in methanol) and the mixture was stirred for 15 minutes. The ethanol was then removed in a rotary evaporator and the remaining 228.3 g of brown liquid was used for distillation in a 15 cm packed column (Braunschweig coils). 201,2 g of main runnings with a boiling point of 67–70° C./0.1 mbar were obtained. The gas chromatographic purity was 98.7%.

Odor description: flowery, like p-tert.butyl cyclohexyl acetate, 25% cis

Example 5

2-(1,1-diethoxyethyl)-naphthalene

Materials:
1) 170.0 g (1.0 mol) p-methylnaphthyl ketone (Aldrich)
2) 177.8 g (1.2 mol) triethyl orthoformate (Fluka)
3) 187.4 mg potassium hydrogen sulfate (Merck)
4) 600 ml ethanol, water-free (technical quality)

Method:
Substances 1) to 4) were introduced into a 1-liter three-necked flask and stirred for 20 hours at 20° C. in the absence of moisture (drying tube filled with silica gel) while dry nitrogen (ca. 2 I/h) was passed through. Thereafter only product could be detected in the mixture by GLC. For working up, the catalyst was neutralized with 2 ml of sodium methylate solution (30% in methanol) and the mixture was stirred for 15 minutes. The ethanol was then removed in a rotary evaporator and the remaining 242.8 g of brown liquid was used for distillation in a 15 cm packed column (Braunschweig coils). 224.3 g of main runnings with a boiling point of 108–110° C./0.1 mbar were obtained. The gas chromatographic purity was 99.4%.

Odor description: cedarwood note, fruity, anthranilate note

Example 6

1-(1,1-diethoxypropyl)-4-methyl benzene

Materials:
1) 99.0 g (0.67 mol) 4-methyl propiophenone (Acros)
2) 121.5 g (0.82 mol) triethyl orthoformate (Fluka)
3) 127.4 mg potassium hydrogen sulfate (Merck)
4) 600 ml ethanol, water-free (technical quality)

Method:
Substances 1) to 4) were introduced into a 1-liter three-necked flask and stirred for 20 hours at 20° C. in the absence of moisture (drying tube filled with silica gel) while dry nitrogen (ca. 2 I/h) was passed through. Thereafter only 10% of educt could be detected in the mixture by GLC. For working up, the catalyst was neutralized with 2 ml of sodium methylate solution (30% in methanol) and the mixture was stirred for 15 minutes. The ethanol was then removed in a rotary evaporator and the remaining 156.0 g of brown liquid was used for distillation in a 15 cm packed column (Braunschweig coils). 110.6 g of main runnings with a boiling point of 62–63° C./0.1 mbar were obtained. The gas chromatographic purity was 93.2%.

Odor description: caraway, tuberose, ylang note, fruity

Example 7

4-tert.butyl-1-(1,1-diethoxyethyl)-benzene

Materials:
1) 49.8 g (0.28 mol) 4-tert.butyl acetophenone (Interchim)
2) 50.0 g (0.34 mol) triethyl orthoformate (Fluka)
3) 52.5 mg potassium hydrogen sulfate (Merck)
4) 300 ml ethanol, water-free (technical quality)

Method:
Substances 1) to 4) were introduced into a 1-liter three-necked flask and stirred for 20 hours at 20° C., in the absence of moisture (drying tube filled with silica gel) while dry nitrogen (ca. 2 I/h) was passed through. Thereafter GLC showed ca. 92% of product in the mixture. For working up, the catalyst was neutralized with 2 ml of sodium methylate solution (30% in methanol) and the mixture was stirred for 15 minutes. The ethanol was then removed in a rotary evaporator and the remaining 75.1 g of brown liquid was used for distillation in a 30 cm packed column (Braunschweig coils). 110.6 g of main runnings with a boiling point of 72–76° C./0.1 mbar were obtained. The gas chromatographic purity was 98.1%.

Odor description: somethat fruity, flowery, woody

What is claimed is:

1. In a perfume composition, the improvement wherein the composition contains at least one phenone ketal having the formula:

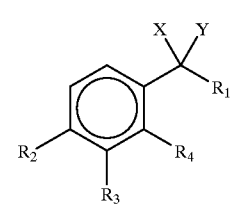

(I)

where X and Y independently of one another represent methoxy, ethoxy, propoxy, or butoxy groups, $R_1$ is a methyl, ethyl, or propyl group, $R_2$ is a hydrogen or a methyl, ethyl, isopropyl, tert. butyl or methoxy group, $R_3$ is hydrogen or a methoxy group, $R_4$ is hydrogen or a methyl group, with the proviso that when X and Y are both methoxy or ethoxy groups, $R_2$ is hydrogen isopropyl, tert. butyl, or methoxy; and wherein at least one of $R_2$, $R_3$, and $R_4$ is other than hydrogen.

2. The perfume composition of claim 1 wherein the at least one phenone ketal is present in from about 1 to about 70% by weight.

3. The perfume composition of claim 1 wherein the at least one phenone ketal is selected from the group consisting of 1-(1,1-diethoxyethyl)-2,4dimethyl benzene, 1-(1,1-diethoxyethyl)3,4dimethoxybenzene, and 1-(1,1-diethoxypropyl)-4 methyl benzene.

4. In a composition containing an odorant, the improvement wherein the odorant comprises at least one phenone ketal of the formula:

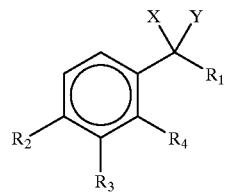
(I)

where X and Y independently of one another represent methoxy, ethoxy, propoxy or butoxy groups, $R_1$, is a methyl, ethyl or propyl group, $R_2$ is hydrogen or a methyl, ethyl, isopropyl, tert.butyl or methoxy group, $R_3$ is hydrogen or a methoxy group, and $R_4$ is hydrogen or a methyl group, with the proviso that when X and Y are both methoxy or ethoxy groups, $R_2$ is hydrogen isopropyl, tent. butyl, or methoxy; and wherein at least one of $R_2$, $R_3$, and $R_4$ is other than hydrogen.

5. The composition of claim 4 wherein the composition is a detergent, cleaner, fabric softener, textile treatment or cosmetic composition.

6. The composition of claim 4 wherein the composition contains from about 0.05 to about 2% by weight of the at least one phenone ketal.

7. The composition of claim 4 wherein the at least one phenone ketal is selected from the group consisting of 1-(1,1diethoxyethyl)-2,4dimethyl benzene, 1-(1,1-diethoxyethyl)-3,4-dimethoxybenzene, and 1-(1,1diethoxypropyl)4-methyl benzene.

8. 1-(1,1-diethoxyethyl)-2,4-dimethyl benzene.

9. 1-(1-diethoxyethyl)-3,4-dimethoxybenzene.

10. 1-(1,1-diethoxypropyl)-4-methyl benzene.

11. In a perfume composition, the improvement wherein the composition contains 1-(1,1-diethoxyethyl)-2,4-dimethyl benzene.

12. In a composition containing an odorant, the improvement wherein the composition contains 1-(1,1diethoxyethyl)-2,4-dimethyl benzene.

13. In a perfume composition, the improvement wherein the composition contains at least one phenone ketal selected from the group consisting of 1-(1,1-diethoxyethyl)-2,4dimethyl benzene, 1(1,1-diethoxyethyl)-3,4dimethoxybenzene, and 1-(1,1diethoxypropyl)-4-methyl benzene.

14. In a composition containing an odorant, the improvement wherein the composition contains at least one phenone Ketal selected from the group consisting of 1-(1,1-diethoxyethyl)-2,4-dimethyl benzene, 1-(1,1-diethoxyethyl) 34-dimethoxybenzene, and 1-(1,1-diethoxypropyl) -4-methyl benzene.

15. In a perfume composition, the improvement wherein the composition contains at least one phenone ketal having the formula:

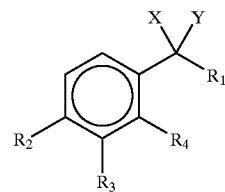
(I)

where X and Y independently of one another represent methoxy, ethoxy, propoxy, or butoxy groups, $R_1$ is a methyl, ethyl or propoxy group, $R_2$ is hydrogen or an ethyl, isopropyl, tert butyl or methoxy group, $R_3$ is hydrogen or a methoxy group, and $R_4$ is hydrogen or a methyl group.

16. In a composition containing an odorant, the improvement wherein the composition contains at least one phenone ketal having the formula:

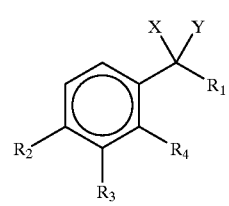
(I)

where X and Y independently of one another represent methoxy, ethoxy, propoxy, or butoxy groups, $R_1$ is a methyl, ethyl or propyl group, $R_2$ is hydrogen or an isopropyl, tert. butyl or methoxy group, $R_3$ is hydrogen or a methoxy group, and $R_4$ is hydrogen or a methyl group, and wherein at least one of $R_2$, $R_3$ and $R_4$ is other than hydrogen.

17. In a perfume composition, the improvement wherein the composition contains at least one phenone ketal having the formula:

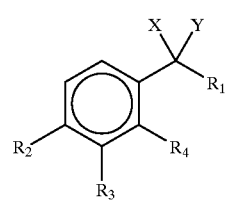
(I)

where X and Y independently of one another represent propoxy, or butoxy groups, $R_1$ is a methyl, ethyl or propyl group, $R_2$ is hydrogen or a methyl, ethyl, isopropyl, tert.butyl or methoxy group, $R_3$ is hydrogen or a methoxy group, and $R_4$ is hydrogen or a methyl group.

18. In a composition containing an odorant, the improvement wherein the composition contains at least one phenone ketal having the formula:

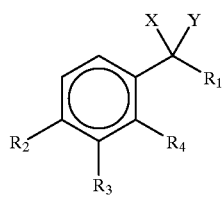

(I)

where X and Y independently of one another represent propoxy, or butoxy groups, $R_1$ is a methyl, ethyl or propyl group, $R_2$ is hydrogen or a methyl, ethyl, isopropyl, tert.butyl or methoxy group, $R_3$ is hydrogen or a methoxy group, and $R_4$ is hydrogen or a methyl group.

19. In a perfume composition, the improvement wherein the composition contains at least one phenone ketal having the formula:

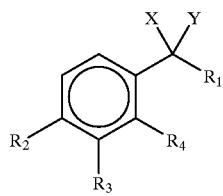

(I)

where X and Y independently of one another represent methoxy, ethoxy, propoxy, or butoxy groups, $R_1$ is an ethyl or propyl group, $R_2$ is hydrogen or a methyl, isopropyl, tert. butyl or methoxy group, $R_3$ is hydrogen or a methoxy group, and $R_4$ is hydrogen or a methyl group.

20. In a composition containing an odorant, the improvement wherein the composition contains at least one phenone ketal having the formula:

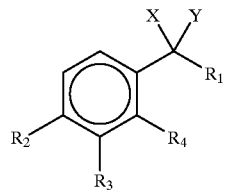

(I)

where X and Y independently of one another represent methoxy, ethoxy, propoxy, or butoxy groups, $R_1$ is an ethyl or propyl group, $R_2$ is hydrogen or a methyl, isopropyl, tert. butyl or methoxy group, $R_3$ is hydrogen or a methoxy group, and $R_4$ is hydrogen or a methyl group.

* * * * *